US00PP15878P3

(12) United States Plant Patent
Meilland

(10) Patent No.: US PP15,878 P3
(45) Date of Patent: Jul. 19, 2005

(54) FLORIBUNDA ROSE PLANT NAMED 'MEIBIONEL'

(50) Latin Name: *Rosa hybrida*
Varietal Denomination: Meibionel

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 66 days.

(21) Appl. No.: 10/727,494

(22) Filed: Dec. 5, 2003

(65) Prior Publication Data

US 2005/0125868 P1 Jun. 9, 2005

(51) Int. Cl.[7] ..... A01H 5/00
(52) U.S. Cl. ..... Plt./150
(58) Field of Search ..... Plt./150

(56) References Cited

U.S. PATENT DOCUMENTS

PP14,245 P3 * 10/2003 Zary ..... Plt./150

PP15,171 P2 * 9/2004 Olesen et al. ..... Plt./150

OTHER PUBLICATIONS http://www.gardenmediagroup.com/Conrad%20Pyle%20New%20Stars%202004.htm.*

* cited by examiner

*Primary Examiner*—Kent Bell
*Assistant Examiner*—W. C. Haas
(74) *Attorney, Agent, or Firm*—Burns, Doane, Swecker & Mathis, LLP

(57) ABSTRACT

A new and distinct variety of rose plant of the Floribunda Class is provided which abundantly forms on a nearly continuous basis attractive double deep scarlet red blossoms that well retain their coloration upon maturity. The growth habit is compact bushy. Very dense dark green semi-matte to semi-glossy foliage is formed that contrasts nicely with the blossom coloration. A well-branched plant develops following budding and grafting. Above average disease tolerance especially with respect to Black Spot is displayed. The new variety is well suited for growing in containers and in smaller gardens.

4 Drawing Sheets

Botanical/commercial classification: *Rosa hybrida*/Floribunda Rose Plant.
Varietal denomination: cv. 'Meibionel'.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) of the new variety was an unnamed selection that resulted from the cross of the 'Meidanu' variety (non-patented in the United States) and the 'Kornita' variety (non-patented in the United States). The male parent (i.e., the pollen parent) was the 'Meifiga' variety (non-patented in the United States). The 'Meidanu' variety has been marketed under the TAMANGO trademark, the 'Kornita' variety has been marketed under the KORONA trademark, and the 'Meifiga' variety has been marketed under the PHARAON trademark. The parentage of the new variety can be summarized as follows:

('Meidanu'×'Kornita')×'Meifiga'.

The seeds resulting from the above pollination were sown and small plants were obtained which were physically and biologically different from each other. Selective study resulted in the identification of a single plant which was the first plant of the new variety.

It was found that the new variety of Floribunda rose plant of the present invention possesses the following combination of characteristics:

(a) exhibits a compact bushy growth habit, (b) forms in abundance in clusters on a nearly continuous basis attractive double deep scarlet red blossoms that well retain their coloration upon maturity, (c) forms very dense dark semi-matte to semi-glossy foliage, (d) develops a well-branched plant following budding and grafting, and (e) exhibits above average disease tolerance for a rose plant of this Class.

The new variety well meets the needs of the horticultural industry. It is particularly well suited for growing in containers and in smaller gardens.

The new variety can be readily distinguished from its antecedent varieties. More specifically, the 'Meidanu' variety forms larger darker red blossoms having more petals on average. The 'Kornita' variety forms smaller blossoms that are orange-scarlet in coloration. The 'Meifiga' variety is a Hybrid Tea that forms significantly larger blossoms that are bright orange-red in coloration.

The new variety has been found to undergo asexual propagation at West Grove, Pa. and at Wasco, Calif. by budding and grafting. Asexual propagation by the above-mentioned methods as performed in Pennsylvania and California has shown that the characteristics of the new variety are stably transmissible from one generation to another.

The new variety has been named the 'Meibionel' variety, and is being marketed under the PREFERENCE trademark.

BRIEF DESCRIPTION OF THE PHOTOGRAPHS

The accompanying photographs show as nearly true as it is reasonably possible to make the same in color illustrations of this character typical specimens of the plant parts of the new variety. The rose plants of the new variety were two years of age and were photographed during September 2003 while growing on 'Dr. Huey' rootstock (non-patented in the United States) at Wasco, Calif. Dimensions in centimeters are included at the bottom of each photograph.

Figure 1:
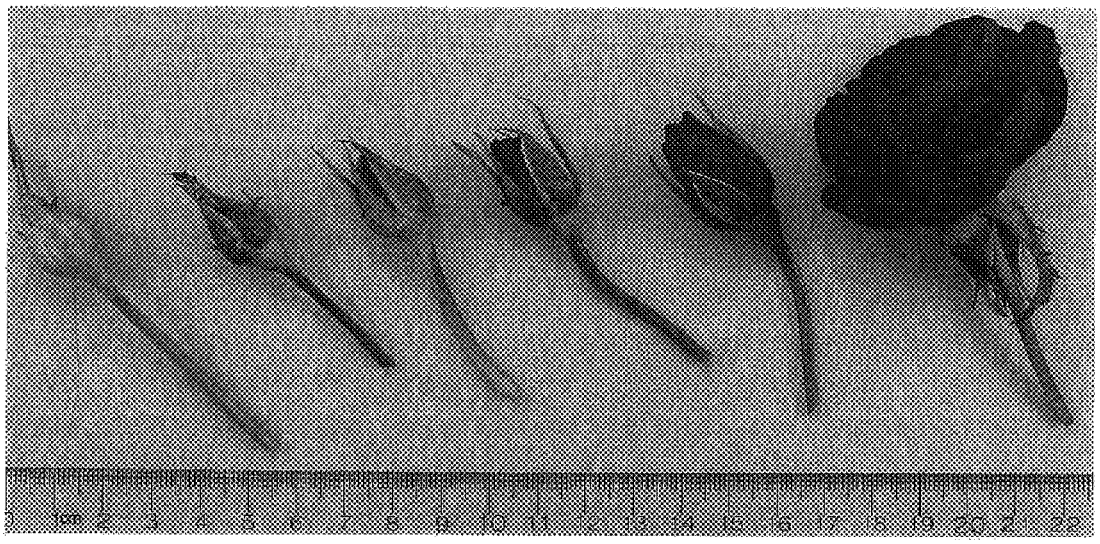
FIG. 1 illustrates a series of six flower buds in progressive stages of opening with an unopened bud being shown at the left and a flower in the course of opening at the right.
Figure 2:
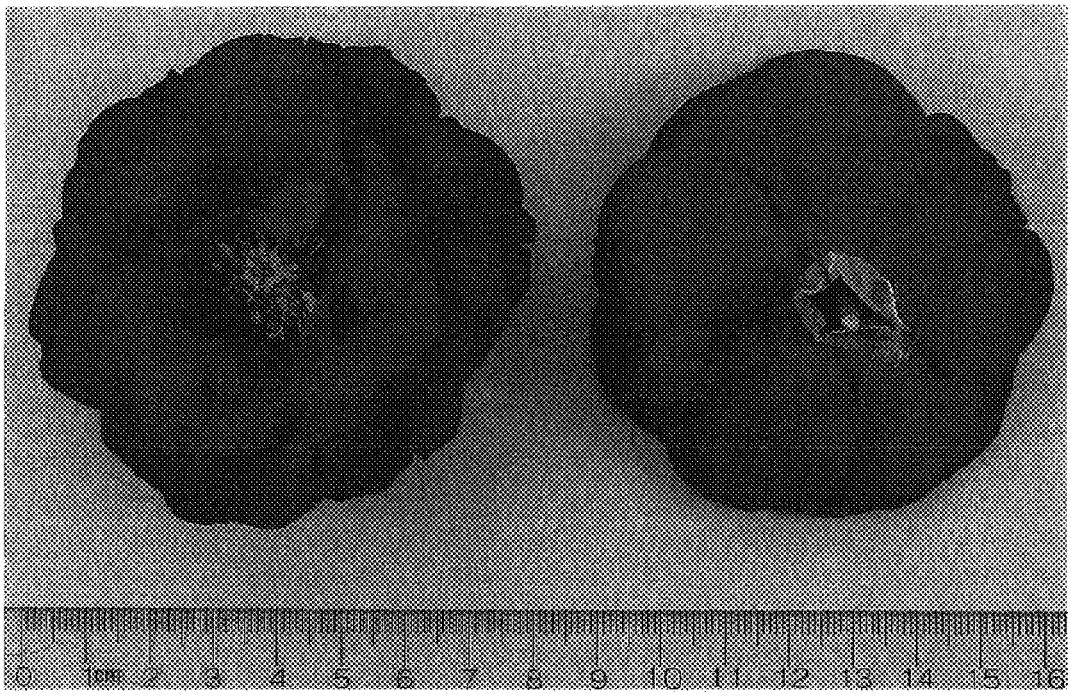
FIG. 2 illustrates open flowers with the obverse being shown at the left and the reverse at the right.
Figure 3:
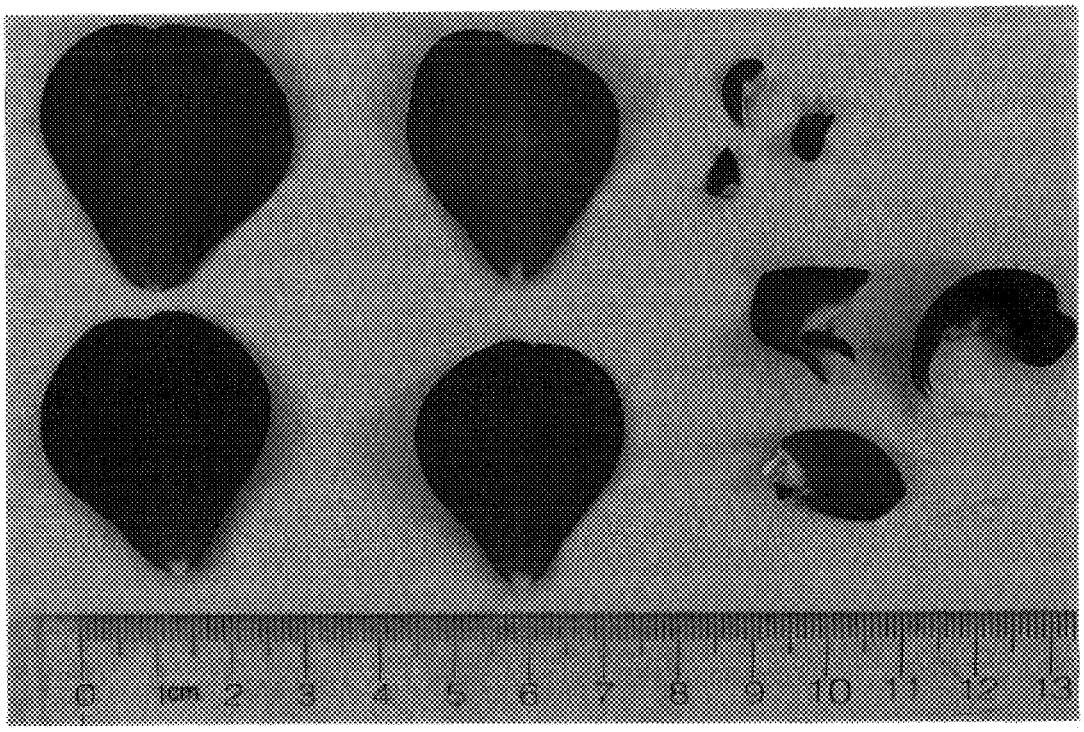

FIG. 3 illustrates typical petals (left) and petaloids (right). The obverse side of the petals is shown above and the reverse side below. Representative sizes and shapes of the petaloids that commonly are displayed are illustrated.

Figure 4:
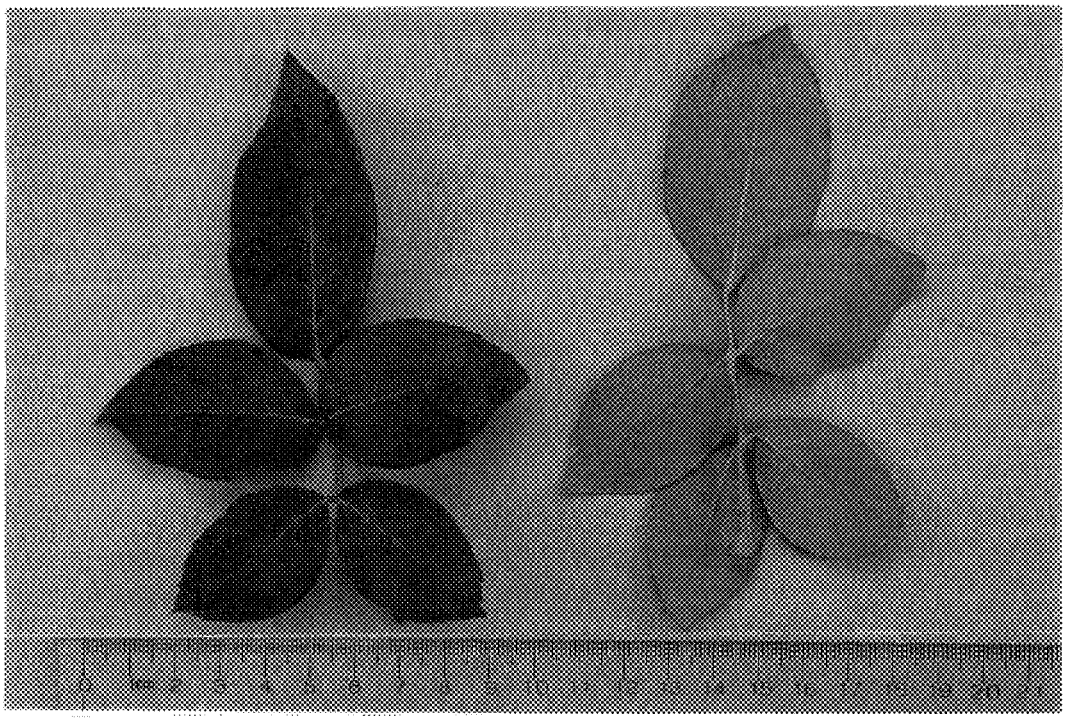

FIG. 4 illustrates typical five-leaflet leaves with the obverse being shown at the left and the reverse at the right.

DETAILED DESCRIPTION

The chart used in the identification of the colors is that of The Royal Horticultural Society (1966 R.H.S. Colour Chart). The description is based on the observation of two-year-old specimens of the new variety which were observed during September 2003 while growing on 'Dr. Huey' rootstock at Wasco, Calif.

Class: Floribunda.

Plant:

*Height.*—Approximately 90 to 120 cm on average at the end of the growing season.

*Width.*—Approximately 60 to 80 cm on average at the end of the growing season.

*Habit.*—Compact bushy.

Branches:

*Color.*—Young stems: near Yellow-Green Group 146B with some lightening to Yellow-Green Group 146C. Adult wood: Yellow-Green Group 146B with some lightening to Yellow-Green Group 146C.

*Thorns.*—On a 15 cm section from a lower section of a flowering stem having a diameter of approximately 11 mm and containing four nodes, there commonly are approximately 10 major prickles having lengths of approximately 5 to 8 mm, approximately 25 minor prickles having lengths of approximately 2 to 5 mm, and over 75 minute prickles less than 2 mm in length that are barely visible but discernible by touch that grade into glandular hairs. On a 15 cm section from an upper section of a flowering stem having a diameter of approximately 6 mm and containing five nodes, there commonly are no major prickles, approximately 5 to 10 minor prickles having lengths of approximately 3.5 to 5 mm, and no minute prickles.

Leaves:

*Shape.*—Alternate and pinnately compound.

*Size.*—The size varies widely within and between leaves of different leaflet numbers. A mature five-leaflet leaf commonly is approximately 9 to 10 cm (approximately 9.5 cm on average) in length, and approximately 6.5 to 7.5 cm (approximately 7.0 cm) in width. A mature seven-leaflet leaf commonly is approximately 11.5 to 16.5 cm (approximately 13.5 cm on average) in length, and approximately 8 to 10.5 cm (approximately 9.3 cm on average) in width.

*Leaflets.*—Number: 3 rarely, and more commonly 5 and 7. Shape: typically broadly elliptical to elliptical to slightly ovate to occasionally oval. Apex: broadly to medium acute to broadly rounded. Base: commonly broadly rounded to oblique to rarely truncate. Texture: stiffly papyraceous, and smooth on both surfaces. Margin: serrate to rarely double serrate. Venation: pinnate, reticulate, and near Yellow-Green Group 145B on both surfaces. General appearance: very dense, dark green, and semi-matte to semi-glossy. Color (adult foliage): Upper surface: near Green Group 139A with some darker shades. Under surface: near Green Group 137C commonly with a distinct matte surface.

Inflorescence:

*Number of flowers.*—Commonly approximately 1 to 6 per inflorescence.

*Peduncle.*—Commonly approximately 3.8 to 6.2 cm (approximately 5.0 cm on average) in length, and approximately 2 to 3 mm (approximately 2.5 mm on average) in diameter.

*Sepals.*—Five in number, and lanceolate commonly with a few foliaceous extensions on two or three sepals.

*Buds.*—Shape: ovoid, approximately 7.5 cm length, approximately 1.5 cm in diameter at the widest point, and near Green Group 143C commonly with some hint of Red-Purple Group 60A towards the peduncle.

*Flower.*—Form: double. Diameter: approximately 6.5 to 8.5 cm (approximately 7.5 on average) when fully open. Depth: commonly approximately 5 to 6 cm. Color when fully open: Upper surface: predominantly near Red Group 53A and lightening continuously near and through Red Group 53B and 53C. Near the petal base near Red Group 51A and Red Group 54A with lightening continuously near and through Red Group 54B and 54C. Veins in the upper and middle areas are near Red Group 45A. At the extreme base of the petals near White Group 155B commonly is displayed. With age increasing amounts of Red-Purple Group 59A. Under surface: near Red Group 53A and lightening continuously near and through Red Group 53B towards the base where Red Group 51A and then near White Group 155B is displayed. With age increasing amounts of near Red-Purple Group 59B and 59C are displayed. Stability of coloration: very good with coloration commonly being well maintained upon full maturity and through petal drop. Petal configuration: typically broadly obovate to occasionally narrowly obovate to turbinate to almost obcordate. Petal number: ranges widely from approximately 12 to 25 under typical growing conditions with an average of approximately 21. Petal arrangement: rosulate. Petal margin: entire though tends to be repand and typically more towards the apex area. Petal apex: typically broadly obtuse to rounded to truncate to emarginated. Petal base: commonly narrowly cuneate to broadly cuneate. Petal size: commonly approximately 30 to 41 mm (average approximately 36 mm) in length, and approximately 21 to 44 mm (average approximately 33.5 mm) in width. Petaloids: commonly approximately 1 to 8 (approximately 4 on average) per bloom. Fragrance: very slight, and so slight that it is impossible to characterize. Pistil number: approximately 70 to 105 (approximately 90 on average). Stigmas: commonly approximately 0.8 to 1.1 (average approximately 1 mm) in size, and near Greyed-Yellow Group 161C in coloration. Styles: commonly approximately 8 to 9.8 cm (averages approximately 8.6 mm) in length, and near Red Group 43C with lightening to near Red Group 43D. Stamen number: commonly approximately 140 to 180. Filaments: commonly approximately 2 to 8 mm in length. Anthers: commonly approximately 1.5 to 2.2 mm (averages approximately 1.8 mm) in size. Receptacle: for a fully open flower approximately 6.5 to 9.5 mm in length, and approximately 7.5 to 8.5 mm in diameter. Petal drop: the petals commonly detach cleanly.

Development:

*Vegetation: Vigorous and strong.*

*Blooming.*—Very abundant and nearly continuous.

*Aptitude to bear fruit.*—None observed.

*Resistance to diseases.*—Above average disease tolerance for a Floribunda is displayed with good resistance to Black Spot.

I claim:

1. A new and distinct variety of Floribunda rose plant characterized by the following combination of characteristics:

(a) exhibits a compact bushy growth habit, (b) forms in abundance in clusters on a nearly continuous basis attractive double deep scarlet red blossoms that well retain their coloration upon maturity, (c) forms very dense dark green semi-matte to semi-glossy foliage, (d) develops a well-branched plant following budding and grafting, and (e) exhibits above average disease tolerance for a rose plant of this Class;

substantially as herein shown and described.

* * * * *